(12) United States Patent
Liu et al.

(10) Patent No.: US 8,017,391 B2
(45) Date of Patent: Sep. 13, 2011

(54) HUMAN LIVER CANCER CELL LINE

(75) Inventors: Chen Liu, Gainesville, FL (US); Alan Hemming, Gainesville, FL (US); Haizhen Zhu, Gainesville, FL (US)

(73) Assignee: Univesity of Florida Research Foundation, Inc., Gainesville, FL (US)

( * ) Notice: Subject to any disclaimer, the term of this patent is extended or adjusted under 35 U.S.C. 154(b) by 43 days.

(21) Appl. No.: 12/282,385

(22) PCT Filed: Mar. 16, 2007

(86) PCT No.: PCT/US2007/006722
§ 371 (c)(1),
(2), (4) Date: Feb. 5, 2009

(87) PCT Pub. No.: WO2007/106596
PCT Pub. Date: Sep. 20, 2007

(65) Prior Publication Data
US 2009/0222933 A1 Sep. 3, 2009

Related U.S. Application Data

(60) Provisional application No. 60/782,832, filed on Mar. 16, 2006.

(51) Int. Cl.
*C12N 5/071* (2010.01)
(52) U.S. Cl. ........................................ 435/370; 435/366

(58) Field of Classification Search ............... 435/370, 435/366
See application file for complete search history.

(56) References Cited

U.S. PATENT DOCUMENTS

2006/0154235 A1 7/2006 Ochiya et al.

OTHER PUBLICATIONS

Wege, H. "Telomerase Reconstitution Immortalizes Human Fetal Hepatocytes without Disrupting their Differentiation Potential" *Gastroenterology*, 2003, pp. 432-444, vol. 124.
Khalil, M. et al. "Human Hepatocyte Cell Line Proliferating as Cohesive Spheroid Colonies in Alginate Markedly Upregulate Both Synthetic and Detoxificatory Liver Function" *Journal of Hepatology*, 2001, pp. 68-77, vol. 297.
Zhong, J. et al. "Robust Hepatitis C Virus Infection In Vitro" *PNAS*, Jun. 28, 2005, pp. 9294-9299, vol. 102, No. 26.
Dash, S. et al. "Transfection of HepG2 Cells with Infectious Hepatitis C Virus Genome" *The American Journal of Pathology*, Aug. 1997, pp. 363-373, vol. 151, No. 2.
Yamashita, Y. et al. "Polyuretane Foam/Spheroid Culture System Using Human Hepatoblastoma Cell Line (Hep G2) as a Possible New Hybrid Artificial Liver" *Cell Transplantation*, 2001, pp. 717-722, vol. 10.

*Primary Examiner* — Thaian N Ton
(74) *Attorney, Agent, or Firm* — Saliwanchik, Lloyd & Eisenschenk (57) ABSTRACT

The present invention relates to a human hepatoma-derived cell line, LH86, liver cell cultures, non-human animal models, artificial livers, liver assist devices, screening assays, and other applications of the cell line as an investigational tool.

10 Claims, 4 Drawing Sheets

LH86 +HCV JFH1

HUMAN LIVER CANCER CELL LINE

CROSS-REFERENCE TO RELATED APPLICATION

This application is the U.S. national stage application of International Patent Application No. PCT/US2007/006722, filed Mar. 16, 2007, which claims the benefit of U.S. Provisional Application Ser. No. 60/782,832, filed Mar. 16, 2006, the disclosures of which are hereby incorporated by reference herein in its their entirety, including any figures, tables, nucleic acid sequences, amino acid sequences, and drawings.

BACKGROUND OF THE INVENTION

The liver performs various functions including the synthesis and secretion of most serum proteins such as albumin and lipoproteins, the synthesis of export lipids coupling to proteins, detoxification, the formation and secretion of bile, blood sugar regulation by the production of sugar, urea synthesis caused by the resulting amino acid degradation, the activation of vitamins, the synthesis and degradation of glycogen, the synthesis of glutathione and metallothionein, and other functions.

Hence, many researchers have cultured liver cells in order to study those functions that are more abundant in liver cells than in other tissue cells, such as their most characteristic ability to synthesize and secrete plasma proteins, and these functions have been utilized for many years.

With the progress of biotechnology, useful substances are actively produced by genetic recombination and cell fusion methods. As a result, animal cell cultivation has become more important than ever. Since the aforementioned abilities of liver cells to synthesize albumin, lipoproteins, export lipids, urea, glycogen, glutathione, metallothionein and the like are more abundant than those of other tissue cells, they are interesting hosts for the production of substance by animal cell cultivation. However, cultivation techniques are not satisfactory at present for maintaining hepatocytes (normal liver cells) capable of producing plasma proteins during cultivation periods.

Normal human hepatocytes are extremely difficult to obtain due to their rapid decrease in viability following autopsy. Additionally, the human liver is one of the few organs in adults capable of regeneration. However, replicative cultures of adult human hepatocytes have never been adequately established, as these cells have a very limited lifespan when put into cell culture.

Many cell lines have serious limitations because they are not of human origin, or are not more closely representative of the normal human liver cell. There are several examples of animal liver cell cultures derived from experimental laboratory animals such as rats (Tsao et. al., *Exp. Cell Res.*, 1984, 154:38-52; Enat et al., *Proc. Nat. Acad. Sci USA*, 1984, 87: 1411-1415). Rat liver epithelial cells from adult rat liver tissue have been established using serum free medium (Chessebeuf and Padieu, *In Vitro*, 1984, 20:780-795; Enat et al., *Proc. Natl. Acad. Sci.*, 1984, 81:1411-1415). Rat liver cells have been transformed by transfection with SV40 DNA (Woodworth et al., *Cancer Res.*, 1987, 46: 4018-4026; Ledley et al., *Proc. Nat. Acad. Sci. USA*, 1987, 84: 5335-5339) but those cells are not suitable for human drug metabolism or carcinogenesis studies because of xenobiotic metabolism differences between rat and human liver cells. Clonally-derived cultures of human hepatocytes have been reported (Kaighn and Prince, *Proc. Nat. Acad. Sci.*, 1971, 68:2396-2400).

Long-Term cultures of human fetal liver have been established (Salas-Prato, M. et al., *In Vitro Cell Dev. Biol.*, 1988, 24:230-238; Sells, M. A. et al., *In Vitro Cell Dev. Biol.*, 1985, 21:216-220); however, the inherent differences between fetal and adult liver, especially in the area of xenobiotic metabolism make adult hepatocytes a more suitable model for carcinogenesis and toxicity studies, for example. Rat liver epithelial cells from adult rat liver tissue have been established using serum-free medium (Chessebeuf and Padieu, *In Vitro*, 1984, 20:780-795; Enat et al., *Proc. Natl. Acad. Sci.*, 1984, 81:1411-1415).

For the purpose of obtaining substitutes for hepatocytes, studies have been actively conducted to create hepatoma cell-derived cell lines that have characteristics peculiar to hepatocytes (normal liver cells) and which are capable of producing liver-specific proteins such as albumin. Hepatoma cells have high proliferation potency and are therefore promising hosts for the production of liver substances. Human hepatoma cell lines have been cultured and are available (e.g., Knowles et al., U.S. Pat. No. 4,393,133, issued Jul. 12, 1983; Knowles B. B. et al., *Science*, 1980, 209:497-499; Monjardino J. and Crawford E., *Virology*, 1979, 96:652-655; Park J. G. et al., *Int. J. Cancer*, 1995, 62:276-282; Zhong et al., *PNAS*, 2005, 102 (26):9294-9299; Fu and Cheng, *Antimicrobial Agents and Chemotherapy*, 2000, 44(12):3402-3407). For example, the human hepatoma cell line, HepG2, is disclosed in U.S. Pat. No. 4,393,133. Further experiments utilizing the HepG2 cell line are reported by Kelly et al., *In Vitro Cell. and Dev. Biol.*, 1989, 25:217-222; U.S. Pat. No. 5,290,684; and Darlington et al., *In Vitro Cell. and Dev. Biol.*, 1987, 2-3:349-354. The human hepatoma cell line, HuH-7, is discussed in Nakabayashi et al., *Cancer Research*, 1982, 42:3858-3863.

Known human-derived hepatoma cell lines include, but are not limited to: HLF (Okayama University, medical school: 1975), HLE, c-1 (Okayama University, medical school: 1975), HuH-6 clone 5 (Okayama University, medical school: 1976), HuH-7 (Okayama University, medical school: 1979), C-HC-4 (Hokkaido University, school of medicine: 1979), HCC-M (Keio University, school of medicine: 1980), JHH-1 (The Tokyo Jikei University School of Medicine: 1980), JHH-2 (The Tokyo Jikei University School of Medicine: 1982), JHH-4 (The Tokyo Jikei University School of Medicine: 1983), KIM-1 (Kurume University, school of medicine: 1983), JHH-5 (The Tokyo Jikei University School of Medicine: 1984), JHH-6 (The Tokyo Jikei University School of Medicine: 1984), OHR (Showa University, school of medicine: 1985), KMCH-1 (Kurume University, school of medicine: 1985), KMG-A (Kurume University, school of medicine: 1985), JHH-7 (The Tokyo Jikei University School of Medicine: 1986), JHC-1 (The Tokyo Jikei University School of Medicine: 1986), KYN-1 (Kurume University, school of medicine: 1986), KYN-2 (Kurume University, school of medicine: 1987), HCC-T (Keio University, school of medicine: 1986), HPT-NT/D3 (Kyushu University, faculty of medicine: 1986), Hep-tabata (Mie University, Faculty of Medicine: 1986), HuCC-T1 (Toyama Medicine and Pharmaceutical University, faculty of medicine: 1987), HuH-28 (Okayama University, medical school: 1987). See HUMAN CELL, Vol. 1, No. 1, p. 106-126, 1988.

Aggressive attempts have also been made to prepare artificial livers by culturing liver cells using bioreactors. The use of artificial support devices has had a dramatic effect on kidney, heart and lung transplantation. Bio-artificial livers (BAL) and other supportive systems for long-term preservation of liver functions have been described (see, for example, Anand A. C., *Indian J. Gastroenterol.*, 2003, 22 Suppl 2:S69-74; Ueda et al., *ASAIO J*, 2003, 49(4):401-6; Tilles et al., *J.*

Hepatobiliary Pancreat. Surg., 2002, 9(6):686-96; Metab. Brain Dis., 2005, 20(4):327-35; and Park and Lee, J. Biosci Bioeng., 2005, 99(4):311-9. Liver assist devices (LAD) have been described previously (see, for example, Lu et al., Tissue Eng., 2005, 11 (11-12):1667-77; Pless and Sauer, Transplant Proc., 2005, 37(9):3893-5; Millis and Losanoff, Nat. Clin. Pract. Gastroenterol Hepatol., 2005, 2(9):398-405; and George J., J. Assoc. Physicians India, 2004, 52:719-22). Such LAD could find application in a number of transplant situations. For example, an artificial liver or LAD could allow patients in fulminant hepatic failure to be stabilized and calmly evaluated before operating; it could stabilize and assist patients after transplant, particularly in situations in which the graph fails to respond on reperfusion; and in some instances it may serve as a substitute for transplant. The device would allow time for the patient's natural liver to regenerate, sparing the expense of operation, the life-long dependence on immunosuppression and the likelihood of premature mortality.

To facilitate the practical use of BAL and LAD, it is desirable to develop a light and small-sized bioreactor apparatus and its peripheral devices. To this end, the creation of cell lines capable of producing the necessary and sufficient amounts of liver-specific proteins in small amounts of media is desired. Human hepatoma cell lines are potentially useful in such systems due to the shortage of normal donors. Investigators have produced a hepatoma cell line potentially useful in BAL systems by overexpressing bcl-2, an anti-apoptosis gene, in hepatoma HepG2 cells (Terada S., J. Biosci. Bioeng., 2003, 95(2):146-51).

Liver cancer is a very common malignancy. Most liver cancers are caused by viral hepatitis viruses, such as hepatitis B virus (HBV) and hepatitis C virus (HCV). Currently, there is no effective therapy.

HCV infection is a major human infectious disease for which there is no effective vaccine. Despite intensive research, the nature of HCV protective immunity is still not well defined. Many lines of evidence suggest the importance of cellular immunity to clear viral infection, but the role of antibody-mediated responses in HCV infection is not known. Most patients with HCV infection have antibodies against viral antigens, but the proportion and strength of the neutralizing antibodies in patient sera are unknown. One limitation to evaluate the nature of neutralizing antibodies is the lack of an infectious cell culture system or small animal model that supports viral infection. Recent success on the cell culture system for one HCV isolate (genotype 2a) has provided a valuable tool to investigate humoral immunity in HCV. It would be advantageous to have available a well-differentiated human hepatoma cell line in which HCV robustly replicates and causes overt cytopathic effects as in nature.

Although there are cell lines derived from human liver cancer, most or all are poorly differentiated and exhibit few liver cell functions. These cell lines are not representative of human tumors. In addition, there is not an efficient cell culture system to culture HBV and HCV, which has dramatically hampered the discovery of antiviral drugs. Although several groups have successfully used primary hepatocyte culture systems and detected low-level replication of HCV, for example, an efficient culture system to grow wild-type HCV has been difficult to achieve (Tagawa M. et al., J. Gastroenterol Hepatol, 1995, 10:523-527; Ito T. et al., J. Gen. Virol., 1996, 77 (Pt. 5):1043-1054; Ito T. et al., Hepatology, 2001, 34:566-572). In 2005, several groups reported the success of cell culture systems that support full HCV production for one particular strain, JFH1, a genotype 2a isolate (Heller T. et al., Proc. Natl. Acad. Sci. USA, 2005, 102:2579-2583; Wakita T. et al., Nat. Med., 2005, 11(7):791-796; Zhong J. et al., PNAs, 2005, 102(26):9294-9; Lindenbach B. D. et al., Science 2005, 309(5734):623-6).

Currently, the only animal model for HCV infection is the chimpanzee (Lanford R. E. et al., Virology, 2002, 293:1-9). On of the primary advantages of the chimpanzee is that it represents a true infection model, though viral pathogenesis may not be identical to human infection (Alter M. J. et al., N. Eng. J. Med., 1999, 341:556-562; Bassett S. E. et al., J. Virol., 1998, 72:2589-2599). The model has provided tremendous knowledge about the host immune responses to HCV infection. The major problems associated with using the chimpanzee model are availability, cost, and resources. Tree shrews (tupaias) are small animals closely related to primates, which adapt easily to a laboratory environment. It has been reported that the tree shrew, Tupaia belangeri, is susceptible to infection with a variety of human viruses in vivo, including hepatitis viruses (die Z. C. et al., Virology, 1998, 244:513-520).

Transgenic mice that express HCV-core protein have been used to study liver pathology and carcinogenesis (Lemon S. M. et al., Trans. Am. Clin. Climatol. Assoc., 2000, 111:146-156). Most of the transgenic lines did not show immediate toxic effect on liver cells, while one transgenic animal line showed lymphocytic infiltration with hepatocyte necrosis (Zhao X. et al., J. Clin. Invest., 2002, 109:221-232). Two other lines showed steatosis and hepatocellular carcinoma (Moriya K. et al., J. Gen. Virol., 1997, 78 (Pt. 7):1527-1531; Moriya K. et al., Nat. Med., 1998, 4:1065-1067). Studies using HBV transgenic mouse models have provided significant insights into HBV immunopathogenesis (Chisari F. V. et al., Science, 1985, 230:1157-1160; Chisari F. V. et al., Hepatology, 1995, 22:1316-1325). However, transgenic models are not yet widely used in studies on HCV immunology. One inherent problem using transgenic mouse models is host immune tolerance to viral proteins, which limits and complicates data interpretation.

It would be advantageous to have available human liver cancer cell lines and animal models that are analogous to the human tumor. Potential applications of such cell lines include, but are not limited to: screening and evaluating anti-tumor drugs; culturing HBV and HCV in a manner resembling the naturally occurring infection; screening and evaluating antiviral drugs; and studying liver cell metabolism.

BRIEF SUMMARY OF THE INVENTION

In one aspect, the present invention pertains to a well-differentiated human hepatoma cell line, referred to herein as the LH86 cell line. In another aspect, the present invention concerns a cell culture comprising cells of the LH86 cell line. In another aspect, the present invention concerns a cell culture comprising cells of the LH86 cell line, wherein the cells are infected with a hepatitis virus, such HBV and/or HCV.

The cell line of the present invention may be used to screen and evaluate anti-tumor drugs; propagate (culture) HBV and HCV in a manner resembling the naturally occurring infection; screen and evaluate antiviral drugs; and study liver cell metabolism. HCV robustly replicates in the cell line. Furthermore, in contrast to cells of the Huh7 or Huh7.5 cell lines, for example, the cells of the present invention exhibit overt cytopathic effects after HCV infection, and the cytopathic effect can be protected by interferon (IFN), or some HCV antiserum.

The cell line of the subject invention can be grown in vitro in a culture growth medium. The cell line may be used for research that will more reliably predict the effect of various chemical assaults on the cell in carcinogen and mutagen research, metabolism research, and other applications for cell lines. Cells of the LH86 cell line have been found to express cytochrome P450 proteins CyP1A1, CyP1B1, and CyP2C9, making these cells particularly useful for drug metabolism studies.

The cell line of the invention can be used in experiments that require large numbers of homogenous (identical and cloned) cells for: drug metabolism studies; evaluating chemical compounds which require liver metabolism for functional activation; chemical carcinogenesis studies with the potential for screening compounds with cancer and/or tumor inhibiting potential; growth of Hepatitis virus in replicating hepatocytes; growth of human parasites; and transfection of additional oncogenes to evaluate their effect on these cells. Cultures of human hepatocytes can provide a more relevant view of human liver metabolism and disease process than data obtained from hepatocyte cultures derived from other animal species.

Cells of the LH86 cell line have been found transform ammonia into urea, which is an important function of the liver. The fact that LH86 cells can metabolize ammonia into urea makes them particularly useful for use in artificial liver devices (i.e., bioartificial livers (BAL) or liver assist devices (LAD)) for clinical or research applications.

Another aspect of the invention includes a non-human animal, comprising cells of the LH86 cell line, which have been implanted or otherwise introduced into the animal. In one embodiment, the non-human animal is a mouse. The non-human animal, which carries cells of the LH86 cell line of the invention, is useful as a model of human liver pathology (e.g., viral infection, liver cancer) and hepatitis virus biology. As indicated above, the LH86 cells of the invention are supportive for the entire HCV life cycle in vivo. The LH86 cells also exhibit overt cytopathic effects by HCV. Thus, the key HCV pathological processes are reproduced in this model, making the animal useful for studying cellular and humoral responses against HCV infection, and in preclinical screening of agents that are candidates for HCV infection prevention (e.g., vaccines) and/or intervention.

DETAILED DISCLOSURE OF THE INVENTION

One aspect of the present invention includes a well-differentiated human hepatoma cell line, referred to herein as the LH86 cell line. The LH86 cell line of the invention was deposited with the American Type Culture Collection (ATCC), 10801 University Boulevard, Manassas, Va. 20110 U.S.A., on Mar. 15, 2006, under the terms and conditions of the Budapest Treaty on the International Recognition of Deposits of Microorganisms for Purposes of Patent Procedure and the Regulations promulgated under this Treaty. The ATCC accession number (Patent Deposit Designation) of the LH86 cell line is PTA-7435.

The ATCC is a depository affording permanence of the deposit and ready accessibility thereto by the public if a patent is granted. All restrictions on the availability to the public of the material so deposited will be irrevocably removed upon the granting of a patent. The material will be available during the pendency of the patent application to one determined by the Commissioner to be entitled thereto under 37 CFR §1.14 and 35 U.S.C. §122. The deposited material will be maintained with all the care necessary to keep it viable and uncontaminated for a period of at least five years after the most recent request for the furnishing of a sample of the deposited cell line, and in any case, for a period of at least thirty (30) years after the date of deposit or for the enforceable life of the patent, whichever period is longer. The applicants' assignee acknowledges its duty to replace the deposit should the depository be unable to furnish a sample when requested due to the condition of the deposit.

In one embodiment (embodiment A), the cell line of the invention is a human liver cell line that exhibits cytopathic effects characteristic of hepatitis C virus (HCV) infection when infected therewith, and that is supportive for the entire HCV life cycle. In a specific embodiment (embodiment B), the cell line is the LH86 cell line having ATCC Accession No. PTA-7435, deposited with the ATCC on Mar. 15, 2006. In another embodiment (embodiment C), the cell line of embodiment A is infected with a microorganism that infects hepatocytes. In another embodiment (embodiment D), the microorganism is a liver pathogen. In another embodiment (embodiment E), the liver pathogen is selected from the group consisting of human immunodeficiency virus (HIV), hepatitis virus, Yellow Fever virus, Dengue virus, Herpes simplex virus (HSV), cytomegalovirus (CMV), Ebola virus, *Helicobacter hepaticus*, and *Plasmodium*. In another embodiment (embodiment F), the liver pathogen is a hepatitis virus selected from the group consisting of as HAV, HBV, HCV, HDV, HEV, HFV, and HGV.

In another aspect, the present invention includes a cell culture comprising cells of the liver cell line according to any one of embodiments A-F.

In another aspect, the present invention includes a non-human animal comprising cells of the liver cell line according to any one of embodiments A-F. In one embodiment (embodiment G), the non-human animal is immune-deficient. In another embodiment (embodiment H), the non-human animal of embodiment a mouse, and can be immune-deficient or non-immune-deficient. In another embodiment (embodiment I), the non-human animal is immune-deficient and is a non-obese diabetic mouse having the severe combined immuno-deficiency mutation (NOD-scid). In another embodiment (embodiment J), the non-human animal of any one of embodiments G-I, the cells of the liver cell line have been administered to the animal in an effective amount to form a tumor.

In another aspect, the present invention includes a method for determining the ability of a substance to exhibit biological activity against the cell line of any of embodiments A-F, comprising: (a) contacting the substance with cells of the cell line; and (b) determining the effect of the substance on the cells. In one embodiment (embodiment K), the method further comprises (c) comparing the effect of the substance on the cells to an appropriate control. In another embodiment of the method (embodiment L), which optionally includes comparing the effect of the substance on the cells to a control, the cells are in cell culture, and the contacting is carried out in vitro. In another embodiment of the method (embodiment M), the cells are carried by a non-human animal, and the contacting is carried out either before the cells are introduced into the animal (in vitro) or after the cells are introduced into the animal (in vivo). In another embodiment of the method (embodiment N), the contacting is carried out after the cells are introduced in the animal (in vivo), and the substance is administered to the animal systemically or locally at the site of the cells. In another embodiment of the method (embodiment O), the method is carried out according to embodiment N, and the animal has a tumor formed by the cells, wherein the substance is administered intra-tumorally. In another embodiment of the method (P), the method is carried out according to any one of the aforementioned embodiments, and the substance is selected from the group consisting of a nucleic acid molecule, polypeptide, and small molecule.

In another aspect, the present invention includes a method for determining the ability of a substance to exhibit biological activity against a liver pathogen, comprising: (a) contacting the substance with cells of the cell line of any one of embodiments D-F, or contacting the substance with a liver pathogen obtained from the cells; and (b) determining the effect of the substance on the pathogen. Optionally, the method further comprises (c) comparing the effect of the substance on the pathogen to an appropriate control. In one embodiment, the substance is selected from the group consisting of a nucleic acid molecule, polypeptide, and small molecule.

One aspect of the present invention concerns a cell culture comprising cells of the LH86 cell line. In another aspect, the present invention concerns a cell culture comprising cells of the LH86 cell line, wherein the cells are infected with one or more virus, bacteria, parasites, or other pathogenic microorganisms, such as human immunodeficiency virus (HIV), hepatitis A virus (HAV), hepatitis B virus (HBV), hepatitis C virus (HCV), *Helicobacter* spp. (such as *H. hepaticus*), etc.

Culturing Procedures/Conditions

The culture media used to prepare the cells described herein can be any physiologically acceptable liquid medium. For example, the cells of the invention can be grown in cell culture using nutrient medium suitable for human hepatoma-derived cell lines. The culture medium can contain various organic and inorganic components that support cell proliferation and may contain various conventional medium components, for example, MEM, DMEM, RPMI 1640, Alpha medium, McCoy's medium, and others.

The cultures could be supplemented with serum, such as those obtained from calf, fetal calf, bovine, horse, human, newborn calf. The serum may be present in the culture in an amount of at least 1% (v/v) to 50% (v/v), preferably the serum concentration is from 5 to 25% (v/v). In an alternative embodiment, the serum can be replaced in whole or in part with one or more serum replacement compositions, which are known in the art.

The cultures are generally maintained at a pH that approximates physiological conditions, e.g., 6.8 to 7.4 and cultured under temperatures of about 37° C. and under a carbon dioxide containing atmosphere, e.g., at least 5%, at least 7%, at least 10%, etc. For example, the cell line can be cultured in a 1:1 mixture of Dulbecco modified Eagle medium and Ham F12 medium (DMEM-F12; SIGMA Chemical Co., St. Louis, Mo.) supplemented with 5% calf serum (HYCLONE Laboratories, Logan Utah) in a humidified atmosphere in 5% $CO_2$ in air at 37° C.

The density of cells in the culture may vary widely and will be dependent on the viability of the cells after initial introduction into the culture system. In one embodiment, the cells are plated and maintained at a cell density of about $5 \times 10^3$ to about $3 \times 10^5$ cells/cm$^2$ in culture medium.

The cell line of the present invention may be used to screen and evaluate anti-tumor drugs; propagate (culture) HBV and HCV in a manner resembling the naturally occurring infection; screen and evaluate antiviral drugs; and study liver cell metabolism. HCV robustly replicates in the cell line. Furthermore, in contrast to cells of the Huh7 or Huh7.5 cell lines, for example, the cells of the present invention exhibit overt cytopathic effects after HCV infection, and the cytopathic effect can be protected by interferon (IFN) or HCV antiserum.

The cell line of the subject invention can be grown in vitro in a culture growth medium. The cell line may be used for research that will more reliably predict the effect of various chemical assaults on the cell in carcinogen and mutagen research, metabolism research, and other applications for cell lines.

The cell line of the present invention may also be used to test the susceptibility of hepatocytes to a viral or non-viral vector of interest, and/or to evaluate the ability of a promoter to drive expression of a transgene within hepatocytes, e.g., tissue-specific expression. Liver-directed gene transfer with viral and non-viral vectors has been explored for the treatment of a variety of inherited and acquired diseases, including hemophilia (Snyder R. O. et al., *Nat. Med.*, 1999, 5:64-70), various metabolic diseases such as mucopolysaccharidosis (Ponder K. P. et al., *PNAS USA*, 2002, 99:13102-13107), hyperlipidemia (Kim I. H. et al., *Hum. Gene Ther.*, 2001, 98:13282-13287), and diabetes mellitus (Kojima H. et al., *Nat. Med.*, 2003, 9:596-603), and chronic viral hepatitis (McCaffrey A. P. et al., *Nat. Biotechnol.*, 2003, 21:639-644). Among the vectors used to deliver genes to hepatocytes in vivo, recombinant adeno-associated virus (rAAV) vectors are one of the most promising vehicles because they are based on non-pathogenic viruses, transducer both dividing and non-dividing cells, and achieve long-term stable transgene expression with minimal toxicity and cellular immune response in mammals.

If the cells of the present invention are to be used to propagate or otherwise provide target cells for microorganisms such as liver pathogens, the nutrient medium employed is a medium sufficient to maintain the cells at temperatures permitting propagation of both the cells and microorganism in the cell culture. Generally, such temperatures range from about 30° C. to about 39° C. Pathogenic and non-pathogenic microorganisms that may be propagated using the cell line of the present invention include, but are not limited to, viruses, bacteria, fungi, and protozoa. Non-limiting examples of liver pathogens include HIV; hepatitis virus, such as HAV, HBV, HCV, hepatitis delta virus (HDV), hepatitis E virus (HEV), hepatitis F virus (HFV), and hepatitis G virus (HGV); Yellow Fever virus, Dengue virus, and other members of the family Flaviviridae that infect hepatocytes; Herpes simplex virus (HSV), such as HSV-1 and HSV-2; cytomegalovirus (CMV);

Ebola virus; members of *Helicobacter*, such as *Helicobacter hepaticus*; and malaria parasites (*Plasmodium*).

Subculturing of the cell culture can generally be carried out utilizing conventional subculturing procedures, e.g., a trypsin procedure described in, for example, Earle W. R., Tissue Culture, Cowdry E. V. ed. Laboratory Technique in Biology and Medicine, 2nd Ed. (1948).

Optionally, microorganism(s) infecting cells of the present invention (e.g., such as hepatitis or other virus) may be harvested in accordance with known techniques employing conventional procedures and reagents to lyse cells containing the microorganism. For example, the preferred method for harvesting the hepatitis A virus is to first allow the infected cells upon reaching confluency to age for approximately two to ten days, and preferably seven days. Following this "aging" period, the growth media is removed from the culture and the cells are lysed. The cell lysates are cleared of nuclei, cell organelles, and debris by centrifugation to yield hepatitis A virus. It has been found that the yields of virus can be increased when the virus-infected cells are lysed utilizing a nonphysiological solution comprising a chelating agent and a nonionic detergent in a buffered solution. The chelating agents and nonionic detergents employed in the methods of the present invention are readily ascertained by one of ordinary skill in the art and include for example, chelating agents such as sodium ethylenediaminetetracetate (EDTA) and non-ionic detergents including, for example, polyethylene glycol p-isooctylphenyl ethers such as Triton X-100 (poly(oxy-1,2-ethanediyl),alpha-[4-(1,1,3,3-tetramethylbutyl)phenyl]-omega-hydroxy-(octoxynol 9)). The hepatitis A virus thus obtained possesses the necessary properties for the preparation of an antigen employed in diagnostic immunoassays, for example.

The cell line of the invention can also be used in experiments that require large numbers of homogenous (identical and cloned) cells for: drug metabolism studies; evaluating chemical compounds that require liver metabolism for functional activation; chemical carcinogenesis studies with the potential for screening compounds with cancer and/or tumor inhibiting potential; growth of Hepatitis virus in replicating hepatocytes; growth of human parasites; and transfection of additional oncogenes to evaluate their effect on these cells. Cultures of human hepatocytes can provide a more relevant view of human liver metabolism and disease process than data obtained from hepatocyte cultures derived from other animal species.

Another aspect of the invention includes a non-human animal, comprising cells of the LH86 cell line, which have been implanted or otherwise introduced into the animal. Preferably, the animal is a non-human mammal, such as a rodent. In one embodiment, the non-human animal is a mouse. In another embodiment, the non-human animal is a tree shrew, *Tupaia belangeri chinensis*. In another embodiment, the non-human animal is a chimpanzee. The non-human animal, which carries cells of the LH86 cell line of the invention, is useful as a model of human liver pathology (e.g., viral infection, liver cancer) and hepatitis virus biology. As indicated above, the LH86 cells of the invention are supportive for the entire HCV life cycle in vivo and the LH86 cells also exhibit overt cytopathic effects by HCV. Thus, the key HCV pathological processes are reproduced in this model, making the animal useful for studying cellular and humoral responses against HCV infection, and in preclinical screening of agents that are candidates for HCV infection prevention (e.g., vaccines) and/or intervention.

Screening Assays

The present invention provides an in vitro method for the screening of substances to evaluate their potential as anti-tumor agents; to evaluate their potential as vaccines or treatments for liver pathogens, such as HAV, HBV, or HCV (e.g., antiviral agents); and/or to evaluate their effect on liver cell metabolism. Assays can be performed on living mammalian cells, which more closely approximate the effects of a particular serum level of the substance in the body, or on extracts prepared from the cultured cell line. Depending upon the purpose of the assay, the cells can be infected with a microorganism of interest (such as HIV, HAV, HBV, HCV, *Helicobacter* spp.).

More specifically, the present invention provides a method of determining the ability of a substance to exhibit biological activity against the cell line or a microorganism infecting the cell line, comprising: (a) contacting the substance to cells of the cell line (optionally, in culture medium) or an extract of the cells; (b) determining the effect of the substance on the cells or the contents of the cell extract (e.g., virus), such as by measuring one or more biological parameters (which may be quantitative, qualitative, or semi-quantitative); and (c) optionally, comparing the effect of the substance on the cells or the contents to a control. Preferably, a pre-selected amount of the substance is used for contacting with the cells of the cell line. The biological parameter may be a parameter of the cells or microorganisms infecting the cells, such as a parameter providing information as to cell growth or growth of the microorganism (e.g., viral growth).

The in vitro method of the invention can be modified such that the effect of the substance on a non-human animal model of the present invention is carried out (in vivo or ex vivo), using the same steps.

Examples of substances that may be evaluated using the methods of the invention include, but are not limited to, nucleic acid molecules, such as DNA encoding polypeptides, interfering RNA, antisense oligonucleotides, ribozymes, triple helices, antibodies or antibody fragments, polypeptides of any length, and small molecules (e.g., small molecule pharmaceuticals or other compounds that are candidates for the treatment of a disease or disorder of the liver (e.g., diseases or disorders caused by pathogenic organisms such as viruses, bacteria, fungi, and protozoans)). Non-limiting examples of liver pathogens include HIV; hepatitis virus, such as HAV, HBV, HCV, hepatitis delta virus (HDV), hepatitis E virus (HEV), hepatitis F virus (HFV), and hepatitis G virus (HGV); Yellow Fever virus, Dengue virus, and other members of the family Flaviviridae that infect hepatocytes; Herpes simplex virus (HSV), such as HSV-1 and HSV-2; cytomegalovirus (CMV); Ebola virus; members of *Helicobacter*, such as *Helicobacter hepaticus*; and malaria parasites (*Plasmodium*).

In one embodiment, the present invention provides methods for screening (both in vitro and in vivo) for substances capable of modulating viral infection (e.g., HCV infection) and/or replication and/or virion assembly. Such methods include administering a candidate substance to virally infected (e.g., HCV) infected or transfected cell line(s) of the invention, and testing for an increase or decrease in a level of viral replication or the expression of a viral protein (e.g., subgenomic HCV replication or HCV-associated protein expression) as compared to a level of viral replication or the expression of a virally related protein (e.g., HCV replication or HCV-associated protein expression) in a control cell line transfected with replication-defective construct or in the same cell line prior to administration of the candidate agent. A decrease in the level of viral replication (e.g., decrease in intra- or extracellular levels of recombinant HCV (+) and/or (−) RNA)) or virally associated protein (e.g., HCV-associated protein expression) would be indicative of the inhibitory activity of the substance with respect to viral replication. Substance-mediated inhibition of virion formation can be detected microscopically (performed directly or after immunostaining); and changes in infectivity of generated virus particles (e.g., HCV particles) can be assayed by isolating them from the cell culture medium and applying to naive cells or a susceptible animal model. Of course, the aforementioned methods can be used for any viral, bacterial, fungal or protozoal liver pathogen (e.g., pathogens including, but not limited to, HIV; hepatitis virus, such as HAV, HBV, HCV, hepatitis delta virus (HDV), hepatitis E virus (HEV), hepatitis F virus (HFV), and hepatitis G virus (HGV); Yellow Fever virus, Dengue virus, and other members of the family Flaviviridae that infect hepatocytes; Herpes simplex virus (HSV), such as HSV-1 and HSV-2; cytomegalovirus (CMV); Ebola virus; members of *Helicobacter*, such as *Helicobacter hepaticus*; and malaria parasites (*Plasmodium*).

In a specific embodiment, HCV-replicating cell lines of the present invention provide a convenient system for high-throughput initial screening of potential anti-HCV vaccines and therapeutics. Such high-throughput screening system involves applying test substances to the microcultures of cell clones supporting subgenomic HCV replication (growing, e.g., in 96- or 324-well microtiter plates) followed by measuring changes (e.g., using multi-plate readers or scanners) in HCV replication and/or HCV-associated protein expression and/or HCV infectivity. According to the instant invention, candidate therapeutic substances include without limitation small molecule enzyme inhibitors (e.g., chelating agents), inhibitory peptides, inhibitory (e.g., transdominant-negative) proteins, antibodies, ribozymes, interfering RNA, DNA encoding a therapeutic polypeptide, small molecule pharmaceuticals, and antisense nucleic acids. Methods used to quantitate HCV (or other liver pathogens of interest) can be incorporated into the screening method and include quantitative RT-PCR (qRT-PCR) for RNA levels and immunological methods for proteins such as ELISA (Rodriguez-Lopez et. al., *J. Gen. Virol*, 1999, 80:727-738, which is incorporated herein by reference in its entirety) or Western analysis (Pietschmann et al., *J. Virol.*, 2001, 75:1253-1264, which is incorporated herein by reference in its entirety).

A further method for screening for agents capable of modulating HCV propagation involves a cell-free system comprising an a cellular extract of the cells of the invention. This method (which can be also performed in a high-throughput format) comprises contacting the in vitro cell-free system of the invention with a candidate substance and testing for an increase or decrease in a level of HCV replication or HCV-associated protein expression compared to a level of HCV replication or HCV-associated protein expression in a control cell-based system or a control cell-free system prior to administration of the candidate agent; wherein a decrease in the level of HCV replication or HCV-associated protein expression compared to the control level is indicative of the ability of the agent to inhibit HCV propagation.

The anti-HCV therapeutic compounds identified using the initial in vitro screening methods of the present invention can be further characterized for their ability to affect subgenomic HCV propagation using secondary screens in cell cultures and/or susceptible animal models. Based on the tropism of the HCV, a preferred small animal model of the present invention is a tree shrew *Tupaia belangeri chinensis*. A preferred large animal model is a chimpanzee. Test animals can be treated with the candidate substances that produced the strongest inhibitory effects in cell culture-based assays (control animals would not be treated, and, if available, a positive control could also be employed). A substance that protects animals from infection by the chimeric virus and/or inhibits viral propagation leading to pathogenicity, would be an attractive candidate for development of an agent for treatment/prevention of HCV infection. In addition, the animal models provide a platform for pharmacokinetic and toxicology studies.

In another embodiment, the cells of the invention are used for screening metabolic compounds or by-products, by identifying substances that affect them. This embodiment comprises incubating substances suspected of affecting liver or hepatocyte function with cells of the invention under conditions sufficient to allow the substance and cells to interact, then subsequently measuring the effect the suspect substance has on cells of the invention. The occurrence of a biological response can be monitored using standard techniques. For example, many biological responses are identified using the level of expression of certain genes in the cell subsequent to incubation. Such genes can include early response genes such as fos, myc or jun (Greenberg, M et. and Ziff, E. *Nature,* 1984, 311:433; eds. Burck, et al., in *Oncogenes,* 1988, Springer-Verlag, New York.). Other genes useful for such studies are known. Techniques that measure the effect of such substances include Northern blot analysis of RNA (transcription), SDS-PAGE analysis of protein (translation), [$H^3$]-thymidine uptake (DNA synthesis) and antibody reactivity (both intracellular and extracellular).

The contacting step in each of the assays (screening methods) described above can involve combining or mixing the substance (such as a chemical compound) and cells of the cell line of the invention, or extracts or microorganisms obtained from the cell line, in a suitable receptacle, such as a reaction vessel, microvessel, tube, microtube, well, or other solid support. The cells and/or substance(s) may be arrayed on a solid support, such as a multi-well plate. "Arraying" refers to the act of organizing or arranging members of a library, or other collection, into a logical or physical array. Thus, an "array" refers to a physical or logical arrangement of, e.g., library members (candidate substances such as chemical compounds). A physical array can be any "spatial format" or physically gridded format" in which physical manifestations of corresponding library members are arranged in an ordered manner, lending itself to combinatorial screening. For example, samples corresponding to individual or pooled members of a substance library can be arranged in a series of numbered rows and columns, e.g., on a multiwell plate. Similarly, cells of the invention can be plated or otherwise deposited in microtitered, e.g., 96-well, 384-well, or -1536 well, plates (or trays). Optionally, cells of the invention may be immobilized on the solid support.

A "solid support" (also referred to herein as a "solid substrate") has a fixed organizational support matrix that preferably functions as an organization matrix, such as a microtiter tray. Solid support materials include, but are not limited to, glass, polacryloylmorpholide, silica, controlled pore glass (CPG), polystyrene, polystyrene/latex, polyethylene, polyamide, carboxyl modified teflon, nylon and nitrocellulose and metals and alloys such as gold, platinum and palladium. The solid support can be biological, non-biological, organic, inorganic, or a combination of any of these, existing as particles, strands, precipitates, gels, sheets, tubing, spheres, containers, capillaries, pads, slices, films, plates, slides, etc., depending upon the particular application. Other suitable solid substrate materials will be readily apparent to those of skill in the art. The surface of the solid substrate may contain reactive groups, such as carboxyl, amino, hydroxyl, thiol, or the like for the attachment of nucleic acids, proteins, etc. Surfaces on the solid substrate will sometimes, though not always, be composed of the same material as the substrate. Thus, the surface can be composed of any of a wide variety of materials, for example, polymers, plastics, resins, polysaccharides, silica or silica-based materials, carbon, metals, inorganic glasses, membranes, or any of the above-listed substrate materials.

The substance in each of the assays (screening methods) described above can be, but is not limited to, nucleic acid molecules, such as DNA encoding polypeptides, interfering RNA, antisense oligonucleotides, ribozymes, triple helices, antibodies or antibody fragments, polypeptides of any length, and small molecules (such as small molecule pharmaceuticals or other compounds that are candidates for the treatment of a disease or disorder of the liver (such as diseases or disorders caused by pathogenic organisms such as viruses, bacteria, fungi, and protozoans)).

In each of the assays (screening methods) described above, the contacting step can be substituted with the step of exposing the cells, cell extract, or microorganism grown using the cells (such as a liver pathogen), to a treatment other than by contact with a substance. Candidate treatments may include exposure to any conditions that potentially have a biological effect on the cells or microorganisms. For example, the treatment may involve exposing the cells, cell extract, or microorganism grown using the cells (such as a liver pathogen) to an energy source, such as a radiation source.

Production of Antibodies

The cells of the present invention may be used to produce antibodies against hepatoma-derived cell lines, such as hepatoma-derived growth factor or hepatopoietin, or against antigens of microorganisms infecting the cells, such as HCV. Antibodies against hepatoma proteins, such as neutralizing antibodies, are known in the art (Nakamura H. et al., *J. Gastroenterol.*, 2002, 37 (Suppl. 14):8-14; Li Y. et al., *DNA and Cell Biology*, 2001, 20(12):791-795). The products of genes differentially expressed in hepatocellular carcinomas represent potential gene products of interest (Paradis V. et al., *American J. Pathology*, 2003, 163(2):733-741; Asada N. et al., *In Vitro Cell. Devl. Biol.-Animal*, 2003, 39:321-328). Neutralizing antibodies, generated through natural infection or either passive or adaptive immunization, are fundamentally important for controlling infectious diseases. Numerous technologies have been developed to produce monoclonal antibodies for diagnosis and clinical therapy (Humphreys D. P. and Gover D. J., *Curr. Opin. Drug. Discov. Devel.*, 2001, 4:172-185; Andersen D. C. and Reilly D. E., *Curr. Opin. Biotechnol.*, 2004, 15:456-462). For the purpose of clinical application, antibody fragments are particularly appealing. Expression of Fab fragments have been carried out in many cells. Mammalian cell cultures, in particular CHO cells, are the most widely used (Dinnis D. M., and James D. C., *Biotechnol. Bioeng.*, 2005, 91:180-189). Humanization of murine monoclonal antibodies, selection of antibodies from phage-display libraries of human antibody fragments, and immunization of transgenic mice carrying human immunoglobulin loci have been used by many investigators. Several therapeutic antibodies have been produced for clinical use (Peterson N. C., *Ilar 1*, 2005, 46:314-319).

For the production of antibodies, various host animals may be immunized by administering them with an immunogenic amount of the gene product of interest (such as an HCV-derived protein), or a portion thereof, isolated from the cells or cell cultures of the invention. Such host animals may include but are not limited to rabbits, mice, and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*.

Monoclonal antibodies may be prepared by using any technique that provides for the production of antibody molecules by continuous cell lines in culture. These include but are not limited to the hybridoma technique originally described by Kohler and Milstein, *Nature*, 1975, 256:495-497, the human B-cell hybridoma technique (Kosbor et al., *Immunology Today*, 1983, 4:72, Cote et al., *Proc. Natl. Acad. Sci.*, 1983, 80:2026-2030) and the EBV-hybridoma technique (Cole et al., 1985, Monoclonal Antibodies and Cancer Therapy, Alan R. Liss, Inc., pp. 77-96). In addition, techniques developed for the production of "chimeric antibodies" (Morrison et al., *Proc. Natl. Acad. Sci.*, 1984, 81:6851-6855; Neuberger et al., *Nature*, 1984, 312:604-608; Takeda et al., *Nature*, 1985, 314:452-454) by splicing the genes from a mouse antibody molecule of appropriate antigen specificity together with genes from a human antibody molecule of appropriate biological activity can be used. Alternatively, techniques described for the production of single chain antibodies (U.S. Pat. No. 4,946,778) can be adapted to produce single chain antibodies specific to one of the binding partners.

Antibody fragments that recognize specific epitopes may be generated by known techniques. For example, such fragments include but are not limited to: the $F(ab')_2$ fragments which can be produced by pepsin digestion of the antibody molecule and the Fab fragments which can be generated by reducing the disulfide bridges of the $F(ab')_2$ fragments. Alternatively, Fab expression libraries may be constructed (Huse et al., *Science*, 1989, 246:1275-1281) to allow rapid and easy identification of monoclonal Fab fragments with the desired specificity.

Antibodies produced using the cells of the invention can be used for diagnostic or clinical purposes. According to the present invention, the usefulness of newly generated antibodies can be assayed by measuring their affinity and specificity (e.g., in the case of antibodies against HCV-derived antigens, upon their application to isolated HCV-derived antigens and/or HCV replicating cell lines of the invention and/or liver tissue sections from chronically infected animals). The anti-HCV antibodies may be used diagnostically, e.g., to detect the presence and/or propagation of HCV in a cell culture or in an animal. Alternatively, these antibodies may be used therapeutically, e.g., in passive immunotherapy.

HCV-specific antibodies prepared according to the invention can be used to detect HCV presence and/or propagation in various biological samples. On the other hand, the invention provides an in vitro method for detecting antibodies to HCV (or other pathogenic microorganism of the liver) in a biological sample from a subject comprising contacting said sample with HCV-replicating cells, cellular fractions, isolated HCV-derived proteins, or HCV-derived viral particles prepared as described above, under conditions that permit interaction of HCV-specific antibodies in the sample with the HCV protein(s), followed by detecting binding of the antibodies in the sample to the HCV-derived protein(s), wherein said binding is indicative of the presence of HCV infection in the subject from which the sample was derived. In the foregoing methods, the biological sample can be derived without limitation from blood, serum, plasma, blood cells, lymphocytes, or liver tissue biopsy. Techniques for isolating proteins and cellular fractions useful in the foregoing diagnostic methods are also well known in the art.

Artificial Liver Devices

The fact that LH86 cells can metabolize ammonia into urea makes them particularly useful for use in artificial liver devices. The cells of the present invention can be used to produce bioreactors, bioartificial livers (BAL), or in liver assist devices (LAD) for clinical, research, or industrial applications (referred to herein collectively and interchangeably as "artificial liver device" or "bio-artificial liver device"). To determine if the cells are expressing and maintaining proper metabolic liver-specific activity, the metabolic functions of the cells can be tested, including the ability to produce human albumin or alpha-1 antitrypsin, perhaps testing oxygen dependence, ability to synthesize glucose and urea, ability to uptake and conjugate bilirubin, and ability to produce clotting factors, for example. Testing is particularly recommended when the cells are to be used in a BAL or LAD.

Cells of the present invention exhibit certain "liver-specific biological activities" including the ability to produce human albumin and alpha-1 antitrypsin. Effecting liver-specific functions is particularly important when the present cells are used in a bio-artificial liver device. Such a device can be used to treat a subject having or suspected of having a liver condition, liver related disorder or compromised liver function resulting either from disease or trauma (e.g., fulminant hepatic failure (FHF), awaiting liver transplant or following liver rejection and awaiting liver retransplant). The term "treat" or "treatment," as used herein, comprises administering to the subject a therapeutically effective amount of blood that has been in contact with serum-free cells of the invention for a time sufficient to cleanse the blood before returning it to the subject. The term "cleanse" or "clean," as used herein, means removal of unwanted or undesired molecules from the subject's blood. Moreover, the term "cleanse" or "clean" further includes the release of desired molecules from cells of the invention into the blood before returning it to the subject. The term "therapeutically effective" as used herein, includes the ability to ameliorate the effects of a liver disorder or compromised liver function in a subject responsive to treatment using cells of the invention. The term "ameliorate" as used herein, refers to a lessening of the condition of the responsive subject. The subject of the treatment is preferably a human, however, it is envisioned that any animal with a liver disorder, liver condition or compromised liver function is treated using cells of the present invention.

Fulminant hepatic failure is a severe hepatocellular dysfunction generally caused by viral hepatitis, drug reactions or poisoning in which encephalopathy typically occurs within eight weeks of the onset of symptoms (Bernau, J. et al, *Sem. Liv. Dis.,* 1986, 6:97-106; Yanda, R. J. West. *J. Med.,* 1988, 149:586-591; Katelaris, P. H. et al., *Med. Clinics N. Amer.,* 1989, 73:955-970). Treatment of FHF or other liver condition, involves culturing cells of the invention in a bio-artificial liver device and cleansing the blood of a subject. The levels of liver-specific biological activity effective to treat or ameliorate a subject suffering from FHF, hepatic failure or compromised liver function are those that result in normal or near normal levels of serum proteins, coagulation factors, amino acids, and other metabolites normally produced in or metabolized by the liver. These various molecules and metabolic products and the physiological as well as pathological ranges of their concentrations or levels are well known and are set forth in Braunwald, E. et al., eds., Harrison's Principles of Internal Medicine, Current Ed., McGraw-Hill, New York, N.Y., incorporated by reference herein.

The liver specific properties of the LH86 cell line make it particularly useful in a bio-artificial liver device by overcoming problems of some other cells used in such devices. Cells are able to duplicate vital biological functions of the liver, and are well differentiated. When used in a bio-artificial liver device, by themselves or cooperating with other cells, the cells of the present invention are capable of carrying out certain liver-specific biological activities at a level effective to support a subject in hepatic failure, or suffering from compromised liver function, for long periods. Thus, the cells of the present invention provide a method for supporting liver function. This provides sufficient time for liver regeneration to occur, as well as providing a better environment for liver regeneration by removing circulating toxins. Furthermore, in those subjects whose livers fail to regenerate, they are kept alive while awaiting transplantation. The method of using cells of the present invention in a bio-artificial liver device also provides a way of allowing subjects to recover after liver failure before transplantation of a first liver. Also, in those subjects who require emergency second transplants, the availability of a bio-artificial liver device allows them to recover before undergoing a second round of major surgery.

When desired, cells of the present invention can be genetically engineered to contain a heterologous nucleic acid sequence whose expression and subsequent functioning can be particularly beneficial to a subject having a liver disorder or suffering from compromised liver function, for example. Membranes or capillaries of a bio-artificial liver device permit cleansing of blood by permitting the crossover of toxic solutes from blood to cells cultured in the device (e.g., dissolved molecular species such as bilirubin diffuse through the membrane and are taken up and metabolized) as well as permitting the diffusion of vital metabolites from cells cultured in the device to blood returning to the subject undergoing treatment. The selectively permeable or semi-permeable character of the membrane of a bio-artificial liver device also provides a mechanical barrier to components of the immune system from the blood of a subject using the device. Typically, the membrane or capillary features a molecular weight cutoff from about 20,000 daltons up to about 80,000 daltons, generally about 30,000 daltons to about 50,000 daltons. In a preferred embodiment, however, the membrane has pores from about 0.1 µm to about 0.3 µm in diameter, typically about 0.2 µm. A pore size diameter in this range excludes cellular elements while permitting proteins and protein complexes to pass through, thus ameliorating serum protein deficiencies of a subject suffering from a liver condition.

Such artificial liver devices, their methods, use and mechanisms of action are commonly known to a person of ordinary skill in the art. Any such device, several designs of which are discussed in the literature, that is capable of culturing or sustaining living cells is contemplated to be used with cells of the invention. In one embodiment, the device comprises cells of the invention (by themselves or in combination with other cells) and a substrate to support the cells (e.g., a cell culture support such as a hollow fiber cartridge, a column, a plate, or a series of hollow fiber cartridges, columns, or plates). In some embodiments, the cells of the invention are arranged as a cell layer and are exposed to circulated fluid such as culture medium, plasma, and/or blood. For example, bio-artificial livers and assist devices are described by Viles et al., U.S. Pat. Nos. 4,675,002 and 4,853,324; Li et al., U.S. Pat. No. 5,270,192; Hu et al., U.S. Pat. No. 5,595,909, U.S. Pat. No. 5,605,835, and U.S. Pat. No. 5,981,211; Talbot et al., U.S. Pat. No. 5,866,420; Amiot, U.S. Pat. No. 5,955,353; Park, U.S. Pat. No. 5,976,870; Kersten et al., U.S. Pat. No. 6,228,607; Triglia et al., U.S. Pat. No. 6,653,105; Myers et al., U.S. Pat. No.

6,858,146; Jauregin, GB 2,221,857A; Wolf et al., *International J. of Artificial Organs*, 1979, 2:97-103; Wolf et al., *International J. of Artificial Organs*, 1978, 1:45-51; Ehrlich et al., *In Vitro*, 1978, 14:443-450, Anand A. C., *Indian J. Gastroenterol.*, 2003, 22 Suppl 2:S69-74; Ueda et al., *ASAIO J.*, 2003, 49(4):401-6; Tilles et al., *J. Hepatobiliary Pancreat. Surg.*, 2002, 9(6):686-96; Park and Lee, *J. Biosci Bioeng.*, 2005, 99(4):311-9; Lu et al., *Tissue Eng.*, 2005, 11 (11-12): 1667-77; Pless and Sauer, *Transplant Proc.*, 2005, 37(9): 3893-5; Millis and Losanoff, *Nat. Clin. Pract. Gastroenterol Hepatol.*, 2005, 2(9):398-405; and George J., *J. Assoc. Physicians India*, 2004, 52:719-22, each of which may be used with the cells of the invention and are incorporated herein by reference. In one embodiment, the bio-artificial liver device includes a hollow fiber cartridge or similar perfusion apparatus having a membrane or capillary as discussed above.

In another embodiment, a bioreactor, such as a hollow fiber bioreactor, can also be utilized as a bio-artificial liver device by permitting cells of the invention to function as a perfused liver. Bioreactors, which employ cartridges or other similar perfusion devices capable of culturing high cell numbers, can replace liver-specific biological activity or allow the accurate assessment of human liver metabolism (as discussed above). Hollow fiber cartridges are two-chamber units that reproduce the three-dimensional characteristics of normal organs (Knazek, R. H., *Feder. Proc.*, 1974, 33:1978-1981; Ku, K. et al., *Biotechnol. Bioeng.*, 1983, 23:79-95, incorporated by reference herein). Culture or growth medium is circulated through the capillary space and cells of the invention, grown in the extracapillary space after seeding, are supplied with a constant inflow of fresh medium (Tharakan, J. P. et al., *Biotechnol. Bioeng.*, 1986, 28:1605-1611. Typically, 1400 cm$^2$ cartridges are inoculated with an effective number of cells (e.g., approximately, 1×10$^9$ cells) and grown to confluence in about 14 to about 21 days. Such hollow fiber culture systems are well known (e.g., Heifetz et al., *BioTechniques*, 1989, 7:192-199; Donofrio, D., *Amer. Biotech. Lab.*, September 1989, Publication #940; incorporated by reference herein) and available commercially.

Hollow fiber based systems when used in a bio-artificial liver device offer several advantages. Cartridges support the growth of very high density cultures. Based on the extracapillary volume, 15 to 20 g of cells are grown in a 1400 cm$^2$ unit and 100 g of cells are grown in a 7000 cm$^2$ unit. This amount of cell mass is capable of providing liver support to a subject suffering from liver failure. Also, cartridge-grown cells are polarized and their growth approximates normal liver structure. The cells receive nutrients from the capillary space and secrete waste products into the extracapillary space. The extracapillary space is perfused to prevent the accumulation of toxic products. The continual flow of media and the in-line oxygenator provide a more constant supply of oxygen and energy.

For the most part, the bio-artificial liver devices contemplated to be used with the cells of the invention primarily process blood by attaching to a subject outside the body (e.g., typically, making fluid communication from the device to the subject's blood supply usually between an artery and a vein). Such an arrangement is particularly useful for providing temporary liver support for subjects suffering from a liver disorder (e.g., FHF). Alternatively, the cell line is used within the body as a bio-artificial liver or as a bio-artificial liver support. When used in this manner, cells of the invention are encapsulated or grown in hollow fiber capillary membranes for internal use. Typically, the cells attach to the support upon growth. Linkage materials, however, may be provided to attach the cells to a support. Cells of the invention can be encapsulated in biomaterial such as alginate-polylysine membranes, as taught by Sun et al., *Trans. Am. Soc. Artif. Intern. Organs*, 1986, Vol. XXXII:39-41; O'Shea et al., *Biochimica Biophysica Acta*, 1984, 804: 133-136; Sun et al., *J. Controlled Release*, 1985, 2:137-141; and U.S. Pat. No. 4,391,909, all of which are incorporated herein by reference. The encapsulated cells and vehicle capsules are then injected intra-peritoneally into the subject.

Additionally, cells of the invention can be used in a synthetic liver-like tissue (an artificial liver tissue) comprising fibroblasts and cells of the invention on a substrate. Typically, co-culture of fibroblasts and hepatocytes do not automatically adopt the arrangement typically found in the liver; and because the two cell types then communicate poorly, the hepatocytes are often functionally inefficient. However, Toner et al., (Fall Meeting of the Materials Research Association, 1-5 Dec. 1997; *Nature*, 1988, 39: 128) describe imprinting a substrate (e.g., borosilicate wafer) using standard photolithographic techniques of microelectronic technology with patterned films of collagen, which promotes cell adhesion. Cells of the invention can then be cultured on such substrates (surfaces), adhering only to the collagen-coated regions. Fibroblasts are then introduced on the bare surface regions producing an intimate mixture of the two cell types in a periodic pattern allowing any ratio of cell types on the substrate permitting adjustment to any physiological value. Using this technique, any pattern size, shape, and number density can be deduced and engineered to order in such an artificial liver tissue.

Genetic Modification

The cells of the present invention can be genetically modified. The term "genetic modification" as used herein refers to the stable or transient alteration of the genotype of a cell of the subject invention by intentional introduction of exogenous nucleic acids by any means known in the art (including for example, direct transmission of a polynucleotide sequence from a cell or virus particle, transmission of infective virus particles, and transmission by any known polynucleotide-bearing substance) resulting in a permanent or temporary alteration of genotype. The nucleic acids may be synthetic, or naturally derived, and may contain genes, portions of genes, or other useful polynucleotides. The term "genetic modification" is not intended to include naturally occurring alterations such as that which occurs through natural viral activity, natural genetic recombination, or the like. The cells of the subject invention can be genetically modified (e.g., genetically engineered) to produce a vast array of biologically active molecules, such as cytokines, growth factors, antigens, receptors, glycoproteins, and enzymes.

Exogenous nucleic acids can be introduced into a cell of the subject invention by viral vectors (retrovirus, modified herpes virus, herpes virus, adenovirus, adeno-associated virus, and the like) or direct DNA transfection (lipofection, calcium phosphate transfection, DEAE-dextran, electroporation, and the like), for example. Liver-specific promoters that may be utilized include, but are not limited to, the human phenylalanine hydroxylase (PAH) gene promoters (Bristeau et al., *Gene* 274:283-291, 2001), hB1F (Zhang et al., *Gene* 273: 239-249, 2001), and the human C-reactive protein (CRP) gene promoter (Ruther et al., *Oncogene* 8:87-93, 1993).

The polypeptides expressed from introduced nucleic acids may be useful in intact host cells; in intact organelles such as cell membranes, intracellular vesicles or other cellular organelles; or in disrupted cell preparations including but not limited to cell homogenates or lysates, microsomes, uni- and multilamellar membrane vesicles or other preparations. Alternatively, the polypeptides can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Finally, high performance liquid chromatography (HPLC) can be employed for final purification steps.

Selectable marker genes encoding enzymes which impart resistance to biocidal compounds may be utilized. Reporter genes can be used for identifying potentially transformed (genetically modified) cells and for evaluating the functionality of regulatory sequences. Reporter genes that encode easily assayable marker proteins are well known in the art. In general, a reporter gene is a gene that is not present in or expressed by the recipient organism or tissue and which encodes a protein whose expression is manifested by some easily detectable property, e.g., enzymatic activity. Preferred genes include the chloramphenicol acetyl transferase gene (cat) from Tn9 of E. coli, the beta-galactosidase gene of E. coli, the beta-glucuronidase gene (gus) of the uidA locus of E. coli, the luciferase gene from firefly Photinus pyralis, and green fluorescent protein (GFP). Expression of the reporter gene is assayed at a suitable time after the DNA has been introduced into the recipient cells.

Other elements such as introns, enhancers, polyadenylation sequences and the like, may also be a part of the recombinant DNA sequence. Such elements may or may not be necessary for the function of the DNA, but may provide improved expression of the DNA by affecting transcription, stability of the mRNA, or the like. Such elements may be included in the DNA as desired to obtain the optimal performance of the transforming DNA in the cell.

The cells of the present invention can be immortalized using methods available for the immortalization or conditional immortalization of mammalian cells. Viral genes, including Epstein-Barr virus (EBV), Simian virus 40 (SV40) T antigen, adenovirus E1A and E1B, and human papilloma virus (HPV) E6 and E7 can induce immortalization by the process of viral transformation. For the most part, these viral genes achieve immortalization by inactivating the tumor suppressor genes that put cells into a replicative senescent state (Hahn, W. C., Mol. Cells, 2002, 13(3):351-361). A preferred method to immortalize cells is through expression of the telomerase reverse transcriptase gene (TERT). The protein product of the TERT gene is inactive in most somatic cells, but when hTERT is exogenously expressed, the cells are able to maintain telomere lengths sufficient to avoid replicative senescence (Bodnar A. G. et. al., Science, 1998, 279(5349) 349-352; Harley C. B., Oncogene, 2002, 21(4):494-502; Rubin H., Nat. Biotechnol., 2002, 20(7):675-681; U.S. Pat. No. 6,261,836; U.S. Pat. No. 6,337,200). Eukaryotic expression plasmids containing hTERT cDNA are commercially available.

As used herein, the term "substance" is intended to refer to any naturally occurring or synthetic material. Examples of substances that may be evaluated using the methods of the invention include, but are not limited to, genetic material, protein, lipid, carbohydrate, small molecules (e.g., small molecule pharmaceuticals or other compounds that are candidates for the treatment of a disease or disorder of the liver (such diseases or disorders caused by pathogenic organisms such as viruses, bacteria, fungi, and protozoans)), a combination of any two or more of the foregoing, or other materials. The substance can be a single material or a mixture. The substances can be obtained from a wide variety of sources including libraries of compounds. Potential substances that may be evaluated using the methods of the invention include, for example, a polypeptide, peptidomimetic, amino acid, amino acid analog, antibody, antibody fragment, polynucleotide, polynucleotide analog, nucleotide, or nucleotide analog. A polynucleotide may encode a polypeptide that potentially exhibits a biological activity on the cells of the cell line, or the polynucleotide may be a short interfering RNA (siRNA), antisense oligonucleotide, ribozyme, triple helix, or other polynucleotide that targets an endogenous or exogenous gene for silencing of gene expression within the cells.

As used herein, the terms "administer", "introduce", "apply", "treat", "transplant", "implant", "deliver", and grammatical variations thereof, are used interchangeably to provide (contact) substances to cells or cultures of the present invention in vitro, or to non-human animals of the present invention in vivo or ex vivo, or to provide the cells of the present invention to a subject or recipient non-human animal, or to provide (contact) substances to microorganisms that have been grown using the cells or cultures of the present invention in vitro or in vivo.

As used herein, the term "isolated" means removal from its native environment, and can include removal from its immediate native environment.

As used herein, the term "culture" is used to denote the maintenance or cultivation of cells in vitro including the culture of single cells. Cultures can be cell, tissue, or organ cultures, depending upon the extent of organization.

As used herein, the term "cell line" is used to refer to cells which have arisen from a primary culture and capable of successful subculture.

As used in this specification, including the appended claims, the singular "a", "an", and "the" include plural reference unless the contact dictates otherwise. Thus, for example, a reference to "a cell" includes more than one such cell.

The terms "comprising", "consisting of" and "consisting essentially of" are defined according to their standard meaning. The terms may be substituted for one another throughout the instant application in order to attach the specific meaning associated with each term.

Unless otherwise defined, all technical and scientific terms used herein have the same meaning as commonly understood by one of ordinary skill in the art of molecular biology. Although methods and materials similar or equivalent to those described herein can be used in the practice or testing of the present invention, suitable methods and materials are described herein.

The practice of the present invention can employ, unless otherwise indicated, conventional techniques of molecular biology, microbiology, recombinant DNA technology, electrophysiology, and pharmacology that are within the skill of the art. Such techniques are explained fully in the literature (see, e.g., Sambrook, Fritsch & Maniatis, Molecular Cloning: A Laboratory Manual, Second Edition (1989); DNA Cloning, Vols. I and II (D. N. Glover Ed. 1985); Perbal, B., A Practical Guide to Molecular Cloning (1984); the series, Methods In Enzymology (S. Colowick and N. Kaplan Eds., Academic Press, Inc.); Transcription and Translation (Hames et al. Eds. 1984); Gene Transfer Vectors For Mammalian Cells (J. H. Miller et al. Eds. (1987) Cold Spring Harbor Laboratory, Cold Spring Harbor, N.Y.); Scopes, Protein Purification: Principles and Practice (2nd ed., Springer-Verlag); and PCR: A Practical Approach (McPherson et al. Eds. (1991) IRL Press)), each of which are incorporated herein by reference in their entirety.

Following are examples that illustrate materials, methods, and procedures for practicing the invention. The examples are illustrative and should not be construed as limiting.

Example 1

LH86 Cells have a Distinctive Morphology

Figure 1A:
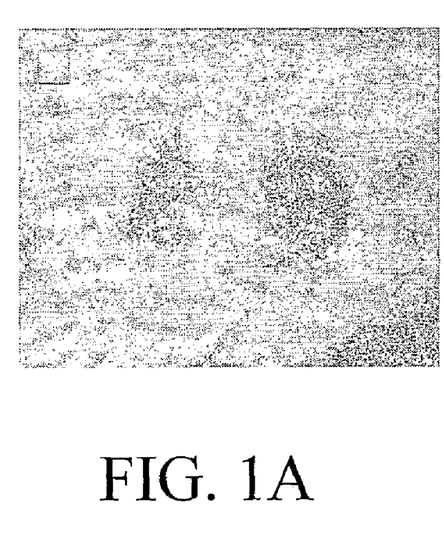
FIGS. 1A-1C show morphology of LH86 cells in culture, at different cell densities. Micrographs were obtained from an inverted microscope.
Figure 1B:
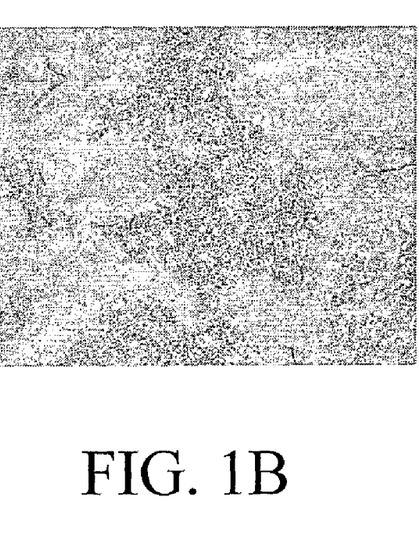
Figure 1C:
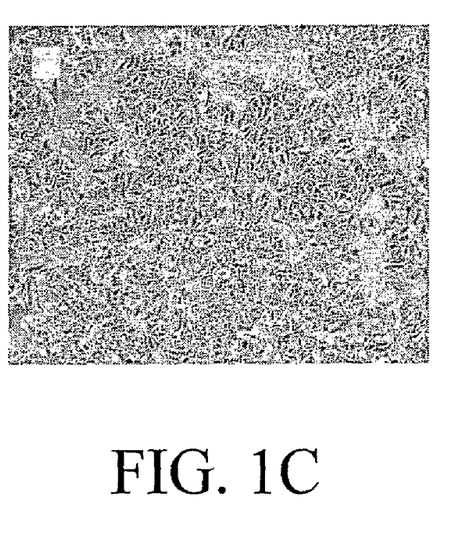

One hepatoma cell line, referred to as LH86, was derived from a patient who has no history of chronic liver diseases or viral infection. The derived cell line, LH86, exhibits a morphology that is distinct from currently existing human hepatoma cell lines, such as Huh7 and HepG2 (FIGS. 1A-1C). The cells form thickened cell cords (more than three-cell layers), resembling thickened liver plates in the original tumor tissue. The cells have a doubling time of approximately 42 hours in the presence of 10 ng/mL EGF.

Example 2

LH86 Cell Line Expresses Liver-Specific Gene Products

Figure 2A:
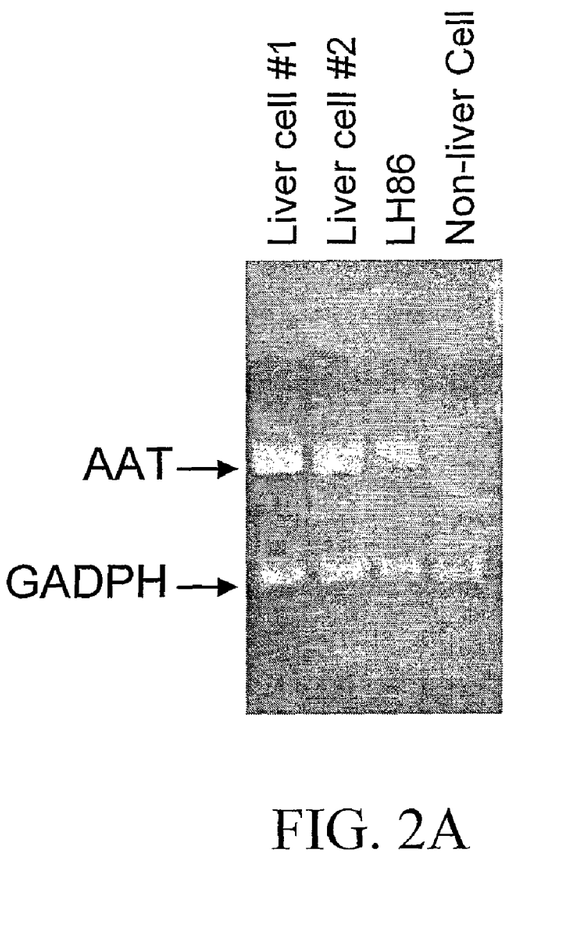
FIGS. 2A-2B show that LH86 cells express liver-specific genes. Total RNA was extracted from LH86 cells, two different other liver cells (#1 and #2), and one non-liver cells, followed by RT-PCR analysis using human alpha-1 antitrypsin primers (FIG. 2A) and albumin primers (FIG. 2B). The amplification products were resolved on 1% agarose gel. GADPH serves as an internal control.
Figure 2B:
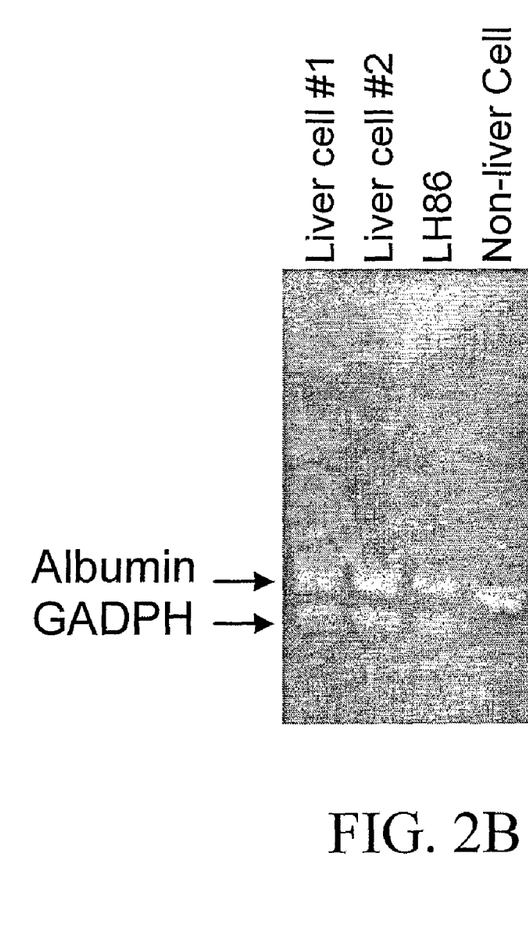

Cells of the LH86 cell line produce abundant human albumin and alpha-1 antitrypsin, which are liver-specific gene products (FIGS. 2A-2B). It appears that the cell line represents a well-differentiated hepatocellular carcinoma. The LH86 cell line has the following HLA genotype: A24/A25, B07.

Example 3

LH86 Cells are Susceptible to HCV and HBV Infection

Figure 3A:
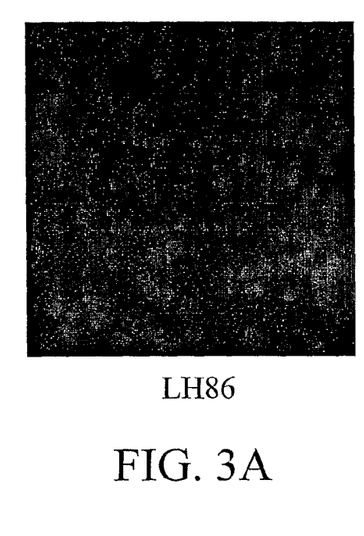
FIGS. 3A-3B show that LH86 cells are susceptible to HCV infection. The cells were immunofluorescently stained with anti-HCV NS5A antibody. The cells were infected for 72 hours.
Figure 3B:
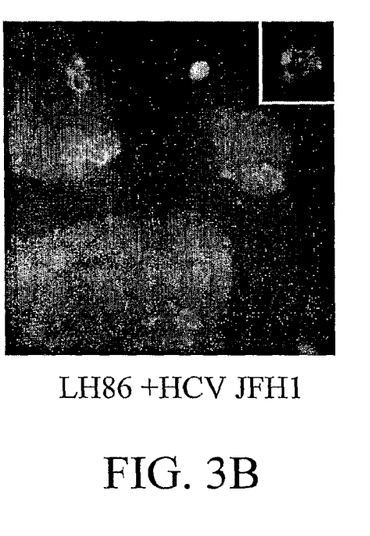
Figure 4:
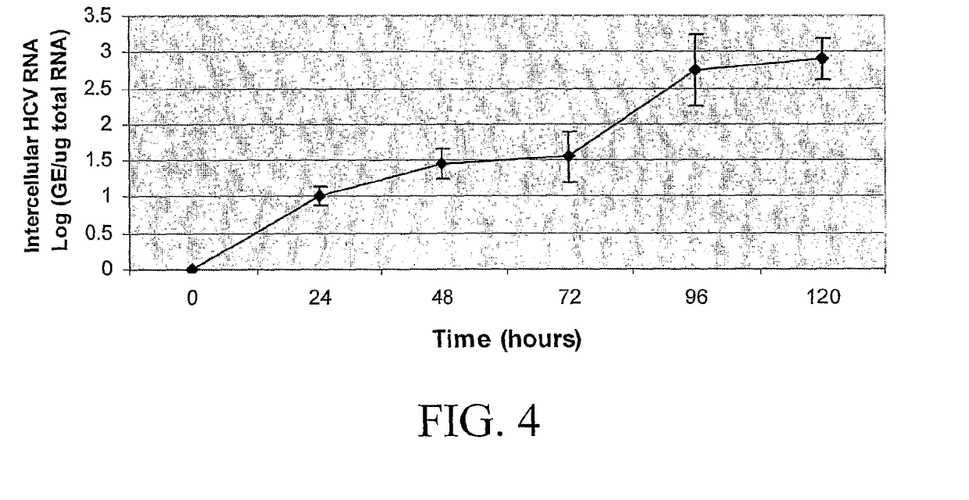
FIG. 4 shows that LH86 cells are susceptible to HCV-JFH1 virus. The LH86-cells were infected by virus released from transfected cells. At the time points indicated, cells were harvested for RNA extraction, followed by real-time RT-PCR analysis with HCV primers. The amount of virus is expressed as genome equivalent (GE) per µg total cellular RNA.
Figure 5:
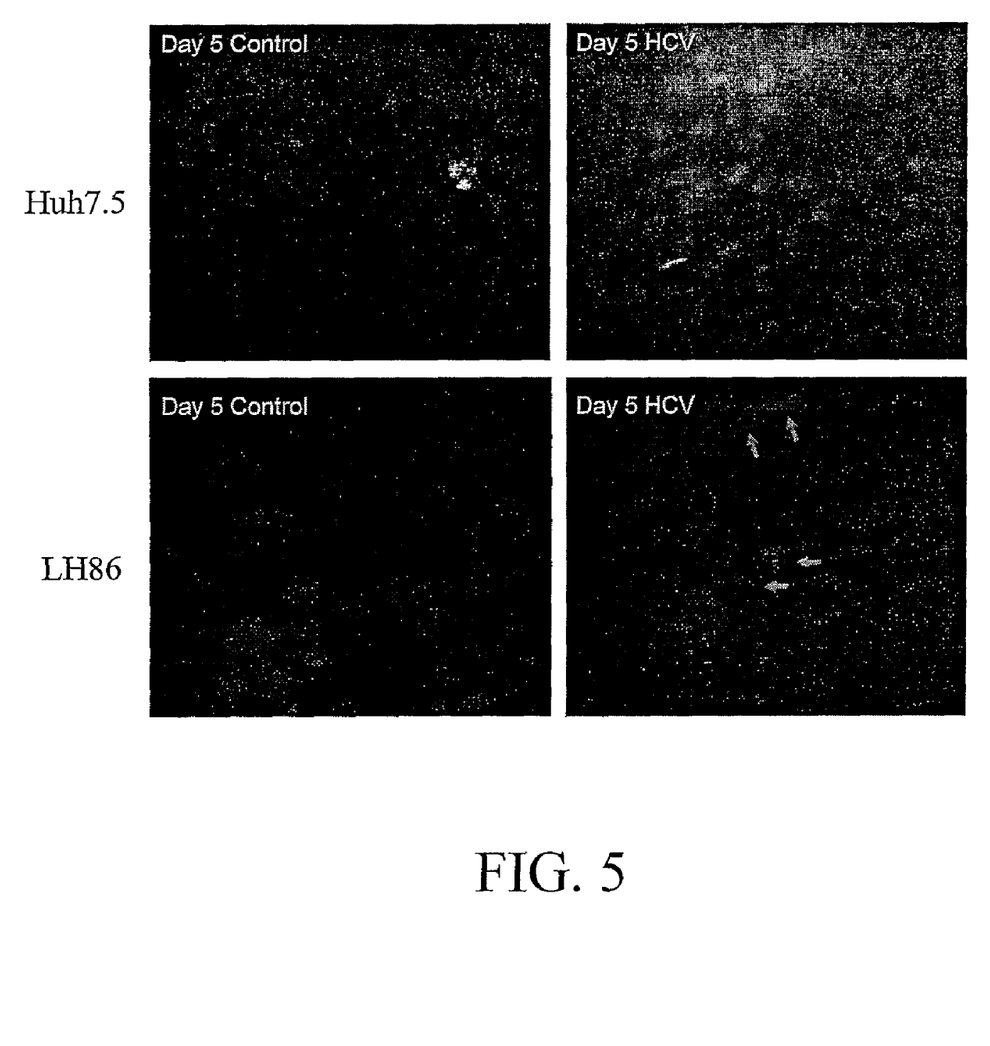
FIG. 5 shows that HCV causes cytopathic effects in LH86 cells. The same amount of virus was inoculated to Huh7.5 and LH86 cells. At day 5, most of the LH86 cells exposed to HCV died, while the control and Huh7.5 cells were normal. A few surviving cells show features of apoptosis (arrows). DAPI stain, 400×.

The present inventors tested the susceptibility of the LH86 cell line to HCV-JFH1 released from Huh7.5 cells. As shown in FIG. 3A-3B and FIG. 4, the cells can be infected by the virus. The present inventors also transfected the cells with HCV-JFH1 RNA transcribed from plasmid pJFH1. It was found that viral particles were released from the cell line and these particles are also infectious to both Huh7.5 cells and LH86 cells. Unexpectedly, however, after 5-6 days of infection, most of the LH86 cells had died. DAPI staining showed that cells underwent nuclear fragmentation, a feature of cell apoptosis (FIG. 5). The viral cytopathic effects were completely inhibited when the cells were pre-treated with 100 U/mL IFN. Infection of Huh7.5 cells did not show overt cytopathic effects, consistent with findings from other groups (Zhong et al., *PNAS*, 2005, 102(26):9294-9299; Cai Z. et al., *J. Virol.*, 2005, 79:13963-13973).

Example 4

Mouse Model for HCV Infection

To establish a mouse model that is capable of supporting the whole viral life cycle, the present inventors implanted HCV susceptible cell lines (LH86 cells of the present invention or Huh7.5 cells) to immune deficient mice (NOD-SCID). When $1 \times 10^6$ cells were injected subcutaneously into the mice, visible tumor (0.5 cm) formed in one week, and the tumor continued to grow to 5 cm in size in 6 weeks. For LH86 cells, $5 \times 10^6$ tumor cells must be injected to achieve a similar tumor growth pattern. Injection of human EGF to mice significantly accelerate tumor growth rate in these mice.

Two experiments were then conducted: (1) injecting tumor cells, followed by HCV-JFH1 viral injection; and (2) injecting HCV-infected tumor cells directly to the mice. Preliminary data indicates that HCV RNA was detectable after 2 weeks, though at a lower level ($2-3 \times 10^3$ GE/mL). Further studies will be carried out to standardize the system.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

We claim:

1. A human liver cell line, wherein the cell line is the LH186 cell line having American Type Culture Collection (ATCC) Accession No. PTA-7435.

2. A human liver cell line that is infected with a microorganism that infects hepatocytes, wherein the cell line is the LH86 cell line having American Type Culture Collection (ATCC) Accession No. PTA-7435.

3. The cell line of claim 2, wherein the microorganism is a liver pathogen.

4. The cell line of claim 3, wherein the liver pathogen is selected from the group consisting of human immunodeficiency virus (HIV), hepatitis virus, Yellow Fever virus, Dengue virus, Herpes simplex virus (HSV), cytomegalovirus (CMV), Ebola virus, *Helicobacter hepaticus*, and *Plasmodium*.

5. The cell line of claim 4, wherein the liver pathogen is a hepatitis virus selected from the group consisting of HAV, HBV, HCV, HDV, HEV, HFV, and HGV.

6. A cell culture comprising cells of the liver cell line according to claim 1.

7. A cell culture comprising cells of the liver cell line according to claim 2.

8. The cell culture of claim 7, wherein the cell line is infected by a microorganism that is a liver pathogen.

9. The cell culture of claim 8, wherein the liver pathogen is selected from the group consisting of human immunodeficiency virus (HIV), hepatitis virus, Yellow Fever virus, Dengue virus, Herpes simplex virus (HSV), cytomegalovirus (CMV), Ebola virus, *Helicobacter hepaticus*, and *Plasmodium*.

10. The cell culture of claim 9, wherein the liver pathogen is a hepatitis virus selected from the group consisting of HAV, HBV, HCV, HDV, HEV, HFV, and HGV.

* * * * *

UNITED STATES PATENT AND TRADEMARK OFFICE
CERTIFICATE OF CORRECTION

PATENT NO. : 8,017,391 B2
APPLICATION NO. : 12/282385
DATED : September 13, 2011
INVENTOR(S) : Chen Liu et al.

It is certified that error appears in the above-identified patent and that said Letters Patent is hereby corrected as shown below:

Cover page:
(73) Assignee, "Univesity" should read --University--.

Column 4,
Line 18, "(die Z." should read --(Xie Z.--.

Column 6,
Line 3, "400x." should read --400 X.--.

Column 11,
Line 47, "comprising an a cellular extract" should read --comprising an acellular extract--.

Column 13,
Line 60, "*Ilar* 1," should read --*Ilar* J.,--.

Column 22,
Line 27, "LH186 cell line" should read --LH86 cell line--.

Signed and Sealed this
Twentieth Day of December, 2011

David J. Kappos
*Director of the United States Patent and Trademark Office*